United States Patent
Amthor et al.

(10) Patent No.: US 11,238,977 B2
(45) Date of Patent: Feb. 1, 2022

(54) AUTOMATED CONSISTENCY CHECK FOR MEDICAL IMAGING

(71) Applicant: KONINKLIJKE PHILIPS N.V., Eindhoven (NL)

(72) Inventors: Thomas Erik Amthor, Hamburg (DE); Jörn Borgert, Hamburg (DE); Joachim Schmidt, Hamburg (DE); Ingmar Graesslin, Boenningstedt (DE); Eberhard Sebastian Hansis, Munich (DE); Thomas Netsch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 16/643,150

(22) PCT Filed: Aug. 28, 2018

(86) PCT No.: PCT/EP2018/073088
§ 371 (c)(1),
(2) Date: Feb. 28, 2020

(87) PCT Pub. No.: WO2019/042969
PCT Pub. Date: Mar. 7, 2019

(65) Prior Publication Data
US 2020/0203002 A1 Jun. 25, 2020

(30) Foreign Application Priority Data
Sep. 1, 2017 (EP) .................................... 17188929

(51) Int. Cl.
*G16H 30/40* (2018.01)
*G16H 30/20* (2018.01)
*G06T 7/00* (2017.01)

(52) U.S. Cl.
CPC ........... *G16H 30/40* (2018.01); *G06T 7/0012* (2013.01); *G16H 30/20* (2018.01);
(Continued)

(58) Field of Classification Search
CPC ........ G16H 30/20; G16H 30/40; G16H 40/40; G06T 7/0012; G06T 2207/10081;
(Continued)

(56) References Cited

U.S. PATENT DOCUMENTS 7,130,760 B2 * 10/2006 Ilic ...................... G06F 11/0709
702/176
8,422,634 B2 * 4/2013 St. John ................. A61B 6/586
378/91

(Continued)

OTHER PUBLICATIONS

PCT International Search Report, International application No. PCT/EP2018/073088, dated Nov. 16, 2018.

*Primary Examiner* — Vu Le
*Assistant Examiner* — Julius Chai
(74) *Attorney, Agent, or Firm* — Larry Liberchuk (57) ABSTRACT

A medical imaging system for acquiring medical image data from an imaging zone. The medical imaging system includes a memory for storing machine executable instructions and medical imaging system commands. The medical imaging system further includes a user interface and a processor. Execution of the machine executable instructions causes the processor to: receive scan parameter data for modifying the behavior of the medical imaging system commands; receive metadata descriptive of imaging conditions from the user interface; store configuration data descriptive of a current configuration of the medical imaging system in the memory; calculate an error probability by comparing the metadata, the configuration data, and the scan parameter data using a predefined model, wherein the error probability is descriptive of a deviation between the metadata and between the (Continued)

configuration data and/or the scan parameter data; perform predefined action if the error probability is above a predetermined threshold.

15 Claims, 5 Drawing Sheets

(52) U.S. Cl.
CPC ............... *G06T 2207/10081* (2013.01); *G06T 2207/10088* (2013.01); *G06T 2207/10116* (2013.01); *G06T 2207/30204* (2013.01)

(58) Field of Classification Search
CPC . G06T 2207/10088; G06T 2207/10116; G06T 2207/30204
See application file for complete search history.

(56) References Cited

U.S. PATENT DOCUMENTS

| | | |
|---|---|---|
| 8,965,080 B2 | 2/2015 | Meetz |
| 2003/0074340 A1* | 4/2003 | Abraham-Fuchs .... G16H 40/67 706/46 |
| 2003/0095144 A1* | 5/2003 | Trevino ............... A61B 5/7475 715/764 |
| 2005/0267348 A1 | 12/2005 | Wollenweber |
| 2007/0016016 A1* | 1/2007 | Haras .................... G06T 7/0012 600/431 |
| 2008/0052112 A1 | 2/2008 | Zahlmann |
| 2009/0292559 A1* | 11/2009 | Ranjan ................... G16H 30/40 705/3 |
| 2011/0176712 A1* | 7/2011 | Hill ........................ G16H 30/40 382/128 |
| 2011/0188718 A1* | 8/2011 | Hill ........................ G16H 30/40 382/128 |
| 2013/0265044 A1 | 10/2013 | Senegas |
| 2013/0311472 A1* | 11/2013 | Cohen-Solal ......... G06F 16/285 707/737 |
| 2015/0196265 A1 | 7/2015 | Suzuki |
| 2015/0216440 A1 | 8/2015 | Senegas |
| 2016/0092748 A1* | 3/2016 | Koktava ............. G06K 9/6201 382/128 |

* cited by examiner

AUTOMATED CONSISTENCY CHECK FOR MEDICAL IMAGING

TECHNICAL FIELD OF THE INVENTION

The invention relates to medical imaging.

BACKGROUND OF THE INVENTION

In various medical imaging modalities, information about the internal structure or anatomical of a subject can be determined non-invasively. For example, a large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. For example, various electrical properties of a subject can be investigated using MRI.

Often times, a physician will order a medical examination of a patient, which will then be conducted by a technician. The technician will acquire and prepare the medical images. Typically, these images will be stored in a format with metadata that provides a context which enables either manual or automated analysis of the medical images. The metadata can contain such information to the orientation of the image, the imaged anatomical regions, and/or conditions which can be important to achieve a correct analysis.

United States patent application US 2013/0265044 A1 discloses a system and method for performing a magnetic resonance imaging scan using a MR scanner. The method can comprise receiving via a user interface a MR imaging protocol categorizable into a MR scan type of a predefined set of MR scan types. Further, the method can comprise querying a database by providing to the database scan information permitting the database to identify the MR scan type of the MR imaging protocol. The method can further comprise receiving from the database statistical information on the MR scan type which can include statistics on modifications of individual scan parameters of the MR scan type, and providing the statistical information to the user interface. Modifications of the MR imaging protocol can be received from the user interface, resulting in a modified MR imaging protocol, according to which the MR imaging scan can be performed.

SUMMARY OF THE INVENTION

The invention provides for a medical imaging system, a computer program product and a method in the independent claims. Embodiments are given in the dependent claims.

Both the acquisition and analysis of medical images is a complicated process. As mentioned above, the analysis or interpretation of the medical images and the acquisition of the images may occur at different times. An automated analysis or manual analysis may rely on the scan parameters of the medical imaging protocol and/or metadata descriptive of the medical image being correct. If either of the scan parameters or the metadata is incorrect or even suspect of being incorrect it may necessitated performing the medical imaging examination again.

Embodiments of the invention may provide for a means of performing a predefined action if there is an inconsistency with either the scan parameters or the metadata. A predefined model may compare scan parameter data and configuration data with metadata to estimate a probability that there is an inconsistency. The scan parameter data is data which may be used for specifying the current medical imaging protocol and configuration of a medical imaging system commands for acquiring medical image data. The configuration data may be data descriptive of the actual electrical and/or mechanical configuration of the medical imaging system. Metadata may include any data entered by the operator which is descriptive of the imaging conditions when the medical image data is acquired. The combination of these distinct sources of information may provide a means to identify inconsistencies which could either lead to substandard imaging and/or incorrectly interpreted medical images.

In one aspect, the invention provides for a medical imaging system for acquiring medical image data from an imaging zone. The medical imaging system comprises a memory for storing machine-executable instructions and medical imaging system commands. The medical imaging system commands are configured for controlling the medical imaging system to acquire medical image data according to a medical imaging imaging protocol. Medical imaging system commands as used herein encompass either the commands or instructions which can be executed by the various components of the medical imaging system to acquire the medical image data. These may be in the form of the actual instructions or data which may be converted into such instructions. For example medical imaging system commands are often found in the form of timing diagrams or groups of sequential commands performed at particular times. An imaging zone as used herein encompasses a region where a subject or part of a subject may be imaged using a radiological imaging modality. In magnetic resonance imaging the imaging zone is a region where a sufficiently high magnetic field and of uniformity of magnetic field exists which enables the acquisition of magnetic resonance data. The imaging zone for a magnetic resonance imaging system is typically generated by a magnet.

The medical imaging system further comprises a user interface. The user interface may be a graphical user interface on a touch screen or other display device. The medical imaging system further comprises a processor for controlling the medical imaging system. Execution of the machine-executable instructions causes the processor to receive scan parameter data for modifying the behavior of the medical imaging system commands. The scan parameter data may for instance be individual modifications to the medical imaging system commands which an operator makes before performing the acquisition of the medical image data. The operator may for example adjust the region of interest or various timing parameters or otherwise modify the particular medical imaging protocol.

Execution of the machine-executable instructions further causes the processor to receive metadata descriptive of the imaging conditions from the user interface. For example the operator may enter various data which may be useful later when interpreting or using medical images generated from the medical image data. This may include such information as the position of the subject being imaged, the weight of the subject, the specific organ or region of interest being imaged and in particular the orientation of the subject with respect to the acquired medical image data. Execution of the machine-executable instructions further causes the processor to store configuration data descriptive of a current configuration of the medical imaging system in the memory. This configuration data may contain all sorts of information descriptive of the state of the medical imaging system before, during or after the medical image data was acquired.

In magnetic resonance imaging, the configuration data for instance may be such data as the type of antenna used for imaging, the position of a subject support supporting a subject within the bore of the magnet of the magnetic resonance imaging system or other data which is descriptive of how the system is electrically and/or mechanically configured.

Execution of the machine-executable instructions further causes the processor to calculate an error probability by comparing the metadata, the configuration data, and the scan parameter data using a predefined model. The error probability is descriptive of a deviation between the metadata and between the configuration data and/or the scan parameter data. In this step the metadata is compared to both the configuration data and/or the scan parameter data. The error probability is used to perform an estimate if either of the metadata or the configuration data or the scan parameter data is an error or conflicting with each other. For instance, when using the medical imaging system an operator may enter incorrect scan parameter data and/or may enter incorrect metadata. The calculation of the error probability may in some examples be considered to be a consistency check.

Execution of the machine-executable instructions further cause the processor to perform a predefined action if the error probability is above a predetermined threshold. The predetermined action comprises providing a signal to notify the user. If the error probability is above the predefined action then the user of the medical imaging system is notified. Execution of the machine-executable instructions further cause the processor to control the medical imaging system to acquire the medical image data from a subject. The performing of the predefined action may be performed before, during and/or after the control of the medical imaging system to acquire the medical image data from a subject. For example, if performing the predefined action is to modify or note that the scan parameters may be incorrect, these may of course be performed before the medical imaging system acquires the medical image data. In the case of indicating that the metadata is incorrect, this may be performed at any time before, during or after the acquisition of the medical image data.

Execution of the machine-executable instructions further causes the processor to receive a response from the user interface in response to the notification signal. Execution of the machine-executable instructions further causes the processor to reconstruct one or more medical images using the medical image data in accordance with the response. Reconstructing the one or more medical images in accordance with the response may take different forms in different examples. If the predefined action was to prompt for confirmation or correction of the scan parameter data, this may be performed before the acquisition of the medical image data. The medical image data is therefore acquired or corrected in accordance with the response. If the predefined action is in response to errors or discrepancies in the metadata then in some examples the metadata may be included into the medical image. The inclusion of this metadata into the medical image may then be performed in accordance with the response.

The present invention pertains to a magnetic resonance imaging system and method and has as an object of the invention to avoid errors, in particular concerns the setting of scan parameters, Notably, the invention aims at setting of scan parameters so that a need for re-examination of the patient to be examined is minimised. According to the invention, this is achieved by way of a consistency check among metadata, configuration data and scan parameter data. Inconsistencies among these datasets may well represent (human) errors in preparing for imaging of the patient to be examined.

More in particular, the metadata are descriptive of the imaging conditions and define aspects of the manner in which the subject is to be imaged as well as aspects of the subject. The metadata further may provide context to enable analysis of the reconstructed magnetic resonance image. For example image segmentation may be supported by the metadata. Examples of the meta data are: orientation of the image and/or of the subject, the anatomical region to be imaged, whether or not a contrast agent is to be administered, scan type, such as type of contrast, which may be reflected in the scan protocol name; also patient age and weight may be included in the meta data.

More in particular, the configuration data are descriptive of the actual mechanical and electrical configuration of the medical image system and are formed by the medical imaging system's settings. The configuration data may be obtained from the medical imaging system's (log) files or by sensors. For example, configuration data may include antenna-positions and orientation, types of transmit and receive coils connected, position of the patient support relative to the medical imaging system's imaging zone, fiducial marker positions representing the position and orientation of the patient (or body parts).

More in particular, the scan parameter data specify the imaging protocol and may also relate to specifying the medical imaging system configuration.

A predefined model may compare scan parameter data and configuration data with metadata to estimate a probability (likelihood) that there is an inconsistency. In general the predefined model represents how metadata, configuration data and scan parameter data form correct combinations or likelihoods of such combinations being correct of incorrect. The predefined model may be implemented in various manners as explained in the description of the invention. A very simple example of an incorrect combination would be to have a knee-coil connected, but no head-coil being connected while the region to be imaged is indicated as the patient's brain. Scores of other and more complicated combinations can be entered in the predefined model.

The consistency check among the metadata, configuration data and scan parameter data returns information on the internal technical status of the medical imaging system. Notably, the information returned is indicative of the metadata, configuration data and scan parameter data being consistent among them. The (degree of) consistency represents the probability (likelihood) of a deviation i.e. an error, among the meta data, configuration data and the scan parameter data. The higher the consistency, the lower the likelihood that an error has occurred; conversely the lower the consistency the higher the likelihood that at least one error has occurred. The deviation or error is found by the comparison of the set of metadata, configuration data and scan parameter to the pre-determined model that represents correct or consistent combinations. Because the predetermined model includes information on correctness and incorrectness of the combinations of metadata, configuration data and scan parameter data, the consistency analyses on the basis co the predetermined model also returns information on the likelihood of metadata, configuration data or scan parameter data being incorrect, i.e. the error probability. The error probability returns a value (between 0 and 1) that represents the likelihood that an error occurs among the metadata, configuration data and scan parameter data. When the error probability is close to zero, then there is almost full consistency among the metadata, configuration data and scan parameter data and almost certainly there is no error. When the error probability is close to one, then there is almost certainly some inconsistency among the metadata, the configuration data and the scan parameter data. The comparison of the predetermined model contain or representing correct combinations of the metadata, the configuration data and the scan parameter data, the consistency analysis also returns a likely error as a notification to the user. Based on the degree of consistency a notification may be issued to the user. Notably, when the error probability exceeds the predetermined threshold, then the medical imaging system is programmed to issue a notification to the user concerning the presumed error among the metadata, configuration data and scan parameter data. These analyses may be carried out before image data acquisition begins so that the likelihood of carrying-out an correct imaging procedure is enhanced.

In another embodiment, the medical imaging system comprises a magnetic resonance imaging system. The medical imaging system commands may be pulse sequence commands. The medical image data may be magnetic resonance data. The medical imaging protocol may be a magnetic resonance imaging protocol.

In another embodiment, the medical imaging system comprises an X-ray machine.

In another embodiment, the medical imaging system comprises a computed tomography system.

In another embodiment, the medical imaging system comprises a PET system.

In another embodiment, the medical imaging system comprises the medical imaging system comprises a SPECT system.

In another embodiment, the predefined action comprises displaying a metadata parameter correction box on the user interface. The metadata parameter correction box may for example be an element on a user interface or graphical user interface which prompts the user to correct at least a portion of the metadata. This embodiment may be beneficial because it may provide for a correction or confirmation of the metadata. It may be impossible to check the accuracy of the metadata at a later time.

In another embodiment, execution of the machine-executable instructions further cause the processor to display the metadata parameter correction box before acquisition of the medical image data. This embodiment may be beneficial because it may force the operator to confirm the accuracy of the metadata before performing the acquisition of the medical image data. This may help to ensure the quality and/or the accuracy of the medical image data that is acquired.

In another embodiment, execution of the machine-executable instructions further causes the processor to display the metadata parameter correction box during the acquisition of the medical image data. This embodiment may be beneficial because the correction or confirmation of the accuracy of the metadata may be performed while the medical imaging system is busy acquiring the medical image data. The operator of the medical imaging system may therefore have several minutes of free time during which the metadata can be reviewed and corrected.

In another embodiment, computation of the error probability comprises comparing a subject orientation in the metadata with an orientation determined from the configuration data. This embodiment may be beneficial because the metadata may be used to provide an orientation to a physician during examination of the medical image data or it may be also used by automatic algorithms for performing such things as segmentations or analysis of the images generated from the medical image data. Confirming the subject orientation in the metadata may therefore reduce the number of times that a medical image needs to be re-acquired because of questions of the accuracy of the metadata or the orientation of the subject within the image.

The configuration data may, for example, be the medical imaging image scan time, a table position of the subject, for example a support which is used to move a subject into the magnetic resonance imaging system may also be indicative of the position of the subject. The type of coil used in magnetic resonance imaging may also be useful in determining this. For example if a head coil is used the region imaged is for example not the thorax. The data acquired by the medical imaging system prior to acquiring the medical image data may also be used as configuration data. For example, there may be one or more segmentations, scout images or other magnetic resonance images which can be used to compare to and also to help provide a reference for or correction for the orientation.

In another embodiment, the computation of the error probability comprises comparing an anatomic region specification in the metadata with an anatomic region determined from the configuration data. An anatomic region specification may for example indicate or label a specific anatomic region within the image or an anatomic component or organ which should be within the image. This embodiment may be beneficial because this sort of metadata may be used to search for images that contain a particular anatomic region. This may facilitate the correct searching of images. Additionally, the metadata descriptive of an anatomic region specification may be used as input or to control automatic segmentation algorithms. Verifying that the anatomic region specification is correct within the metadata may help automatic segmentation algorithms to function properly.

The configuration data which may be useful in determining an anatomic region may include, but are not limited to: a medical imaging scan time, a table position, a type of coil or antenna used, and data from one or more segmentations or prior magnetic resonance images, prior medial images, and combinations thereof.

In another embodiment, execution of the machine-executable instructions further cause the processor to display a set of suggested metadata corrections in the metadata parameter correction box. This may be beneficial because it may help the operator to recognize an error in the metadata and/or may help the operator to correct the metadata.

In another embodiment, the predefined action comprises displaying a scan parameter correction box on the user interface. The scan parameter correction box may comprise a prompt to correct at least one scan parameter. Execution of the machine-executable instructions cause the processor to display the scan parameter correction box before acquisition of the medical image data. This embodiment may be beneficial because correcting the scan parameters before the acquisition of the medical image data may eliminate or prevent the need to re-acquire the medical image data later.

In another embodiment, execution of the machine-executable instructions further causes the processor to display a set of suggested scan parameter corrections in the scan data parameter correction box. This embodiment may be beneficial because it may help the operator to correctly correct the scan data before the medical image data is acquired.

In another embodiment, the metadata comprises a subject orientation of the subject. The subject orientation may include the up-down and left-right position or orientation of the subject relative to an imaging plane which may be reconstructed from the medical image data.

The metadata may also further comprise a subject age of the subject. This for example can be compared to the size and/or weight of the subject. The metadata may further comprise a subject weight of the subject. The weight of the subject may be useful in performing various applications in the classification of images or correctly interpreting them.

In magnetic resonance imaging, the metadata may further comprise a specification if the magnetic resonance image was acquired with or without a contrast agent present. This metadata may be useful in algorithms which are used for comparing images before and after the contrast agent was administered.

The metadata may further comprise a scan type of the medical imaging protocol. The specification of a scan type may be useful because sometimes the medical imaging protocol is classified by scan type but the actual scan that was used for this protocol is different than its intended use. Having a proper scan type may therefore be useful in properly interpreting the medical image. A scan name of the medical imaging protocol may also be useful metadata. For example, the scan name can be tokenized and parsed and this information can also be compared against scan parameters and/or a state of the medical imaging system.

In another embodiment, the configuration data comprises a connected coil type for magnetic resonance imaging. The coil may for example be a magnetic resonance imaging coil or antenna. The type of coil that is connected may be useful in determining the type of data or magnetic resonance data that was acquired from the subject. The configuration data may also comprise an image of the body position of the subject. For example a camera could be used to take an image of the body position of the subject. This information could be used manually to confirm data or image recognition could be used to roughly interpret the position of the subject. Such images may also be used in producing an estimate of the bulk and/or weight of a subject.

The configuration data may further comprise a fiducial marker position of a fiducial marker on the subject. This may also be useful in determining the orientation or location of a subject in the image. The configuration data may further comprise a weight sensor data descriptive of the weight of the subject. A knowledge of the weight may be useful in determining or interpreting the medical imaging data properly also. The configuration data may further comprises data from the survey magnetic resonance image or scout magnetic resonance images of the subject. These may be used for determining accurately the position of the subject and/or the location of certain anatomical structures that may be imaged by the magnetic resonance data that was acquired.

The configuration data may also further comprise an applied dose for a CT or an X-ray system for irradiating the subject. The configuration data may further comprise a subject weight of the subject. This may also be useful in interpreting the medical image data properly. The configuration data may also further comprise a subject support position of the subject support in the medical imaging system. The location of the subject support may be useful in estimating what anatomy is within the imaging zone. This may provide a rough check of the anatomy or region of the subject being imaged.

In another embodiment, the one or more medical images comprises the metadata. For example various image formats enable the embedding of the metadata directly within an image. Having the corrected metadata incorporated into the image may provide for a more useful medical image.

In another embodiment, execution of the machine-executable instructions further causes the processor to construct a DICOM image using the at least one image and the metadata. This embodiment may be beneficial because this metadata may make the DICOM image more useful and ensure the quality of when the images are processed.

Execution of the machine-executable instructions further cause the processor to segment the one or more medical images using an automatic segmentation algorithm. The automatic segmentation algorithm is at least partially configured to use the metadata. For example the patient orientation and/or table position may be used to start an automatic segmentation correctly.

In another embodiment, the predefined model is a decision tree. For example the decision tree may be used to directly compare various pieces of metadata with the scan parameter and a configuration data directly. In another embodiment, the predefined model comprises a statistical likelihood model. This embodiment may be beneficial because the statistical likelihood of various scan parameter data, metadata, and configuration data can be compared directly to generate a probability.

In another embodiment, the predefined model comprises a principal component analysis model. This embodiment may also be beneficial because it may provide for an effective means of calculating the error probability.

In another embodiment, the predefined model comprises a machine learning model. This embodiment may be beneficial because it may provide for a gradual improvement of the calculation of the error probability as the medical imaging system is used more. For example, the feedback from displaying the metadata parameter correction box or the scan parameter correction box may be used to directly improve the performance of the machine learning model. Likewise a neural network could also be used in place of the machine learning model to provide such continually improving calculation of the error probability.

In another aspect, the invention provides for a computer program product comprising machine-executable instructions for execution by a processor controlling the medical imaging system. The medical imaging system is configured for acquiring medical image data from an imaging zone. The medical imaging system comprises a user interface. Execution of the machine-executable instructions causes the processor to receive scan parameter data for modifying the behavior of medical imaging system commands. The medical imaging system commands are configured for controlling the medical imaging system to acquire the medical image data according to a medical imaging protocol.

Execution of the machine-executable instructions further cause the processor to receive metadata descriptive of imaging conditions from the user interface. Execution of the machine-executable instructions further cause the processor to store configuration data descriptive of a current configuration of the medical imaging system in a memory. Execution of the machine-executable instructions further cause the processor to calculate an error probability by comparing the metadata, the configuration data, and the scan parameter data using a predefined model. The error probability is descriptive of a deviation between the metadata and between the configuration data and/or the scan parameter data. Execution of the machine-executable instructions further cause the processor to perform a predefined action if the error probability is above a predetermined threshold. The predetermined action comprises providing a signal to notify the user.

Execution of the machine-executable instructions further cause the processor to control the medical imaging system to acquire the medical image data from a subject. Execution of the machine-executable instructions further cause the processor to receive a response from the user interface in response to the signal that notifies the user. Execution of the machine-executable instructions further cause the processor to reconstruct one or more medical images from the medical image data in accordance with the response.

In another aspect, the invention provides for a method of operating a medical imaging system. The medical imaging system is configured for acquiring medical image data from an imaging zone. The medical imaging system comprises a user interface. The method comprises receiving scan parameter data for modifying the behavior of medical imaging system commands. The medical imaging system commands are configured for controlling the medical imaging system to acquire the medical image data according to a medical imaging protocol. The method further comprises receiving metadata descriptive of imaging conditions from the user interface. The method further comprises storing configuration data descriptive of a current configuration of the medical imaging system in a memory. The method further comprises calculating an error probability by comparing the metadata, the configuration data, and the scan parameter data using a predefined model. The error probability is descriptive of a deviation between the metadata and between the configuration data and/or the scan parameter data. The method further comprises performing a predefined action if the error probability is above a predetermined threshold. The predetermined action comprises providing a signal to notify the user.

The method further comprises controlling the medical imaging system to acquire the medical image data from a subject. The method further comprises receiving a response from the user interface in response to the signal that notifies the user. The method further comprises reconstructing one or more medical images from the medical image data in accordance with the response. Providing a signal to notify the user may for example be the displaying of the metadata parameter correction box on the user interface or the displaying of the scan parameter correction box on the user interface.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging system. A medical imaging system is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance data is an example of a medical image data. A magnetic resonance imaging system is an example of a medical imaging system. Magnetic Resonance (MR) data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two or three dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

In the illustrated examples, specific reference is made to a magnetic resonance imaging system. It is understood that the figures below are used to also discuss medical imaging systems such as PET systems, SPECT systems, CT systems, and X-ray systems in general. As such, references to a magnetic resonance imaging system can also be understood to be descriptive of a medical imaging system. References to pulse sequence commands can also be understood to be descriptive of medical imaging system commands. The medical image data may be References to magnetic resonance data can also be understood to be descriptive of medial image data. References to a magnetic resonance imaging protocol can also be understood to be descriptive of a medical imaging protocol.

Figure 1:
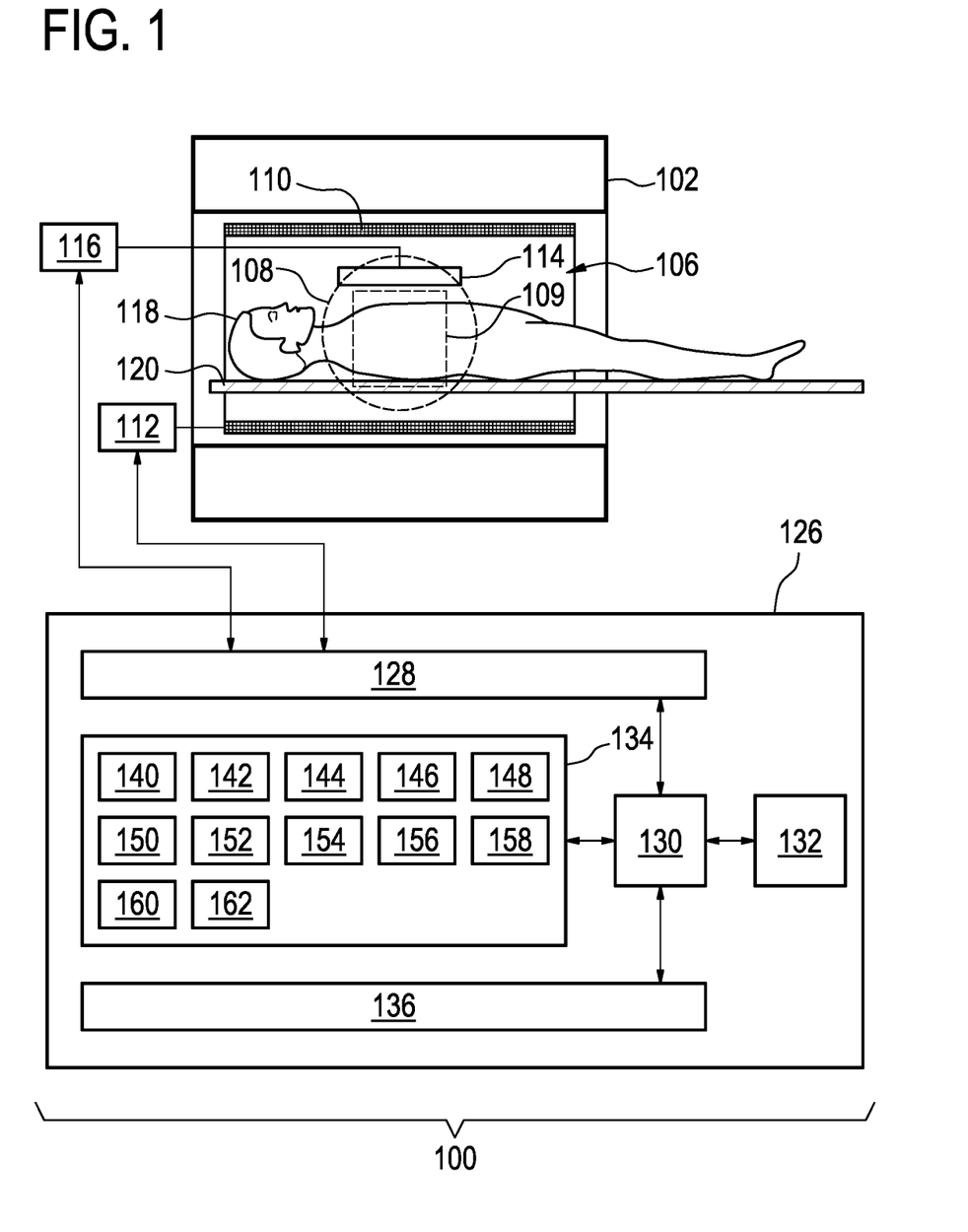
FIG. 1 illustrates an example of a magnetic resonance imaging system.

FIG. 1 illustrates an example of a magnetic resonance imaging system 100. The magnetic resonance imaging system comprises a magnet 102. The magnet 102 may for example be a superconducting magnet. Alternatively, the magnet 102 may be a resistive type magnet.

The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 102 there is an imaging zone 108 where the magnetic field is strong and uniform enough to perform magnetic resonance imaging. A region of interest 109 is shown within the imaging zone 108. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 102. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for receiving radio transmissions from spins also within the imaging zone 108. In some examples, the radio-frequency coil may also be configured for manipulating the orientations of magnetic spins within the imaging zone 108. The radio frequency antenna may contain multiple coil elements. The radio frequency antenna may also be referred to as a channel or antenna. The radio-frequency coil 114 is connected to a radio frequency receiver or transceiver 116. The radio-frequency coil 114 and radio frequency transceiver 116 may be optionally replaced by separate transmit and receive coils and a separate transmitter and receiver. It is understood that the radio-frequency coil 114 and the radio frequency transceiver 116 are representative. The radio-frequency coil 114 could also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116, the gradient controller 112, current source 124, and magnet power supply 104 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples, the memory 130 may be a non-transitory computer-readable medium.

The processor 130 is further shown as being connected to an optional network interface 136. The network interface 136 may be used to connect the computer system 126 to other computers and/or database systems. The processor 130 is shown as being connected to the display 132. The display 132 may for example be used to provide a graphical user interface or other interface for displaying and/or receiving data from an operator.

The memory 134 is shown as containing machine-executable instructions 140. The machine-executable instructions 140 enable the processor 130 to control the operation and function of the magnetic resonance imaging system 100. The memory 134 is further shown as containing pulse sequence commands 142. The pulse sequence commands 142 enable the processor 130 to control the magnetic resonance imaging system 100 to acquire magnetic resonance data. The memory 134 is further shown as containing magnetic resonance data 144 that was acquired by controlling the magnetic resonance imaging system 100 with the pulse sequence commands 142.

The memory 134 is further shown as containing scan parameter data 146 that was used to modify the pulse sequence commands 142 before the magnetic resonance data 144 was acquired. The memory 134 is further shown as containing metadata 148 that is descriptive of the magnetic resonance data 144. The metadata 148 could have been received for example from the display 132. The memory 134 is further shown as containing configuration data 150 that is stored in the memory 134. The configuration data 150 may be data that is logged by the processor 130 and is descriptive of a state of the magnetic resonance imaging system 100 when the magnetic resonance data 144 is acquired. This may include such things as position of the subject support 120, the type of antenna 114 used or other data. The memory 134 is further shown as containing an error probability 152 that was calculated using a predefined model 154. The error probability 152 is a probability that the metadata 148 is inconsistent with the scan parameter data 146 and/or the configuration data 150.

The memory 134 is shown as containing a predetermined threshold 156. The error probability 152 is compared to the predetermined threshold 156. If the error probability 152 or one of the probabilities calculated is greater than the predetermined threshold 156, this may indicate that the metadata 148, the configuration data 150, and/or the scan parameter data 146 has an error within it. If the error probability 152 is above the predetermined threshold 156 the processor 130 executes the commands 158 which cause the computer system 126 to generate a signal to notify an operator. The signal may for instance be in the form of information or a user interface which is displayed on the display 132. In other examples, there may be lights, vibrating, or audible signals which are also generated.

The memory 134 is shown as further containing a response 160 from the user interface 132 that was received in response to the generation of the signal 158 notifying the user. The response 160 may for instance be data which is used to correct or modify the metadata 148 or the scan parameter data 146. In some instances, the response is simply a certification that the metadata 148 and/or the scan parameter data 146 is indeed correct. The memory 134 is further shown as containing a magnetic resonance image 162 that was reconstructed from the magnetic resonance data 144. In some examples the metadata 148 may be incorporated into or included as metadata in the magnetic resonance image 162.

Figure 2:
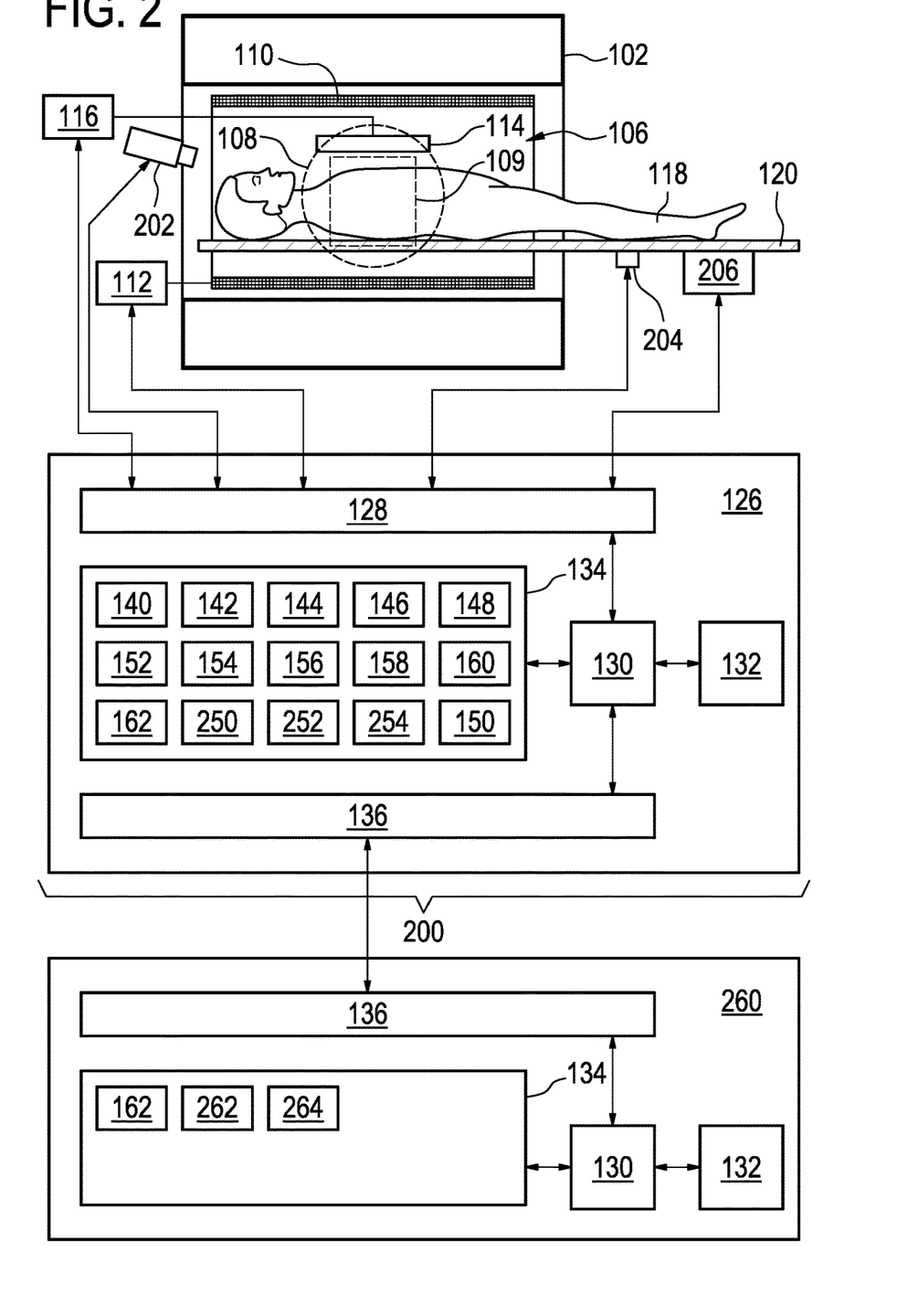
FIG. 2 illustrates a further example of a magnetic resonance imaging system.

FIG. 2 shows a further example of the magnetic resonance imaging system 200. The magnetic resonance imaging system 200 in FIG. 2 is similar to that shown in FIG. 1. There is additionally a camera 202 which is able to acquire images of the subject 118 when the subject 118 is within the bore 106 of the magnet 102. The magnetic resonance imaging system 200 of FIG. 2 is also additionally shown as containing a weight sensor 204 for measuring the weight of the subject 118 when the subject 118 is on the subject support 120. The magnetic resonance imaging system 200 of FIG. 2 is also additionally shown as comprising a subject support actuator 206 which is able to move the subject support 120 into a particular position within the bore 106 of the magnet 102. The hardware interface 128 is additionally shown as being able to exchange data with the camera 202, the weight sensor 204, and the subject support actuator 206. The computer memory 134 shows additional types of configuration data 150. There is camera data 250 that is acquired with the camera 202, weight sensor data 252 that has been acquired with the weight sensor 204 and table position data 254 which is received from the subject support actuator 206. The camera data 250, the weight sensor data 252, and the table position data 254 are additional data which can be compared to the metadata 148 to ensure that the metadata 148 is correct. Values or information determined from the camera data 250, the weight sensor data 252, the table position data 254 or other configuration 150 could be used at least partially by the predefined model 154 to calculate the error probability 152.

The network interface 136 of the computer system 126 is shown as being connected to a network interface 136 of a workstation 260. The workstation also comprises a processor 130, a display 132 and a memory 134. The memory 134 of the workstation 260 is shown as containing the magnetic resonance image 162. It has been transferred via the network interfaces 136. The workstation's 260 memory 134 may contain a segmentation algorithm 262 that uses the image 162 and combined metadata to generate an image segmentation 264. The segmentation algorithm 262 may use input from the metadata that is stored within the magnetic resonance image 162 to function or start the segmentation algorithm properly.

Figure 3:
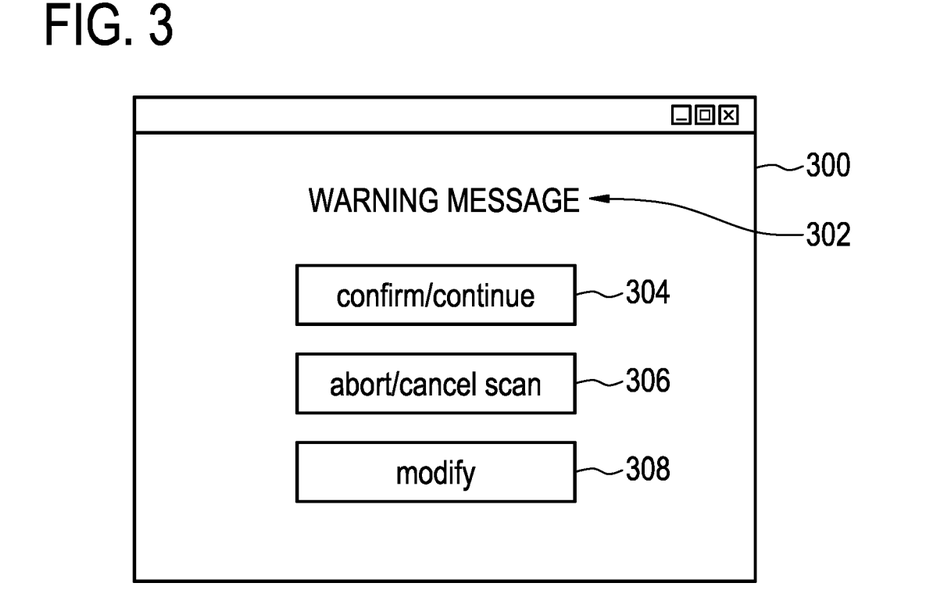
FIG. 3 illustrates an example of a graphical user interface.

FIG. 3 shows an example of a metadata parameter correction box or a scan parameter correction box 300. This box 300 may be displayed as part of a graphical user interface. The box 300 comprises a warning message 302 that is generated as part of the predefined action. The generation of the box 300 may also be part of the predefined action. In this example the box is shown as having three controls 304, 306 and 308. Control 304 is a button which can be clicked to confirm the accuracy of the metadata and/or the scan parameters. When box 304 is clicked the operation of the magnetic resonance imaging system continues as normal. In some examples there may be a log entry indicating that the warning message 302 was displayed and the operator confirmed that both the metadata and/or the configuration data was indeed correct. Box 306 contains a button or control which clicked aborts or cancels the scan or the acquisition of the magnetic resonance data. The button 308 contains another button which opens a dialogue and may enable the operator to correct the metadata and/or the scan parameters.

Figure 4:
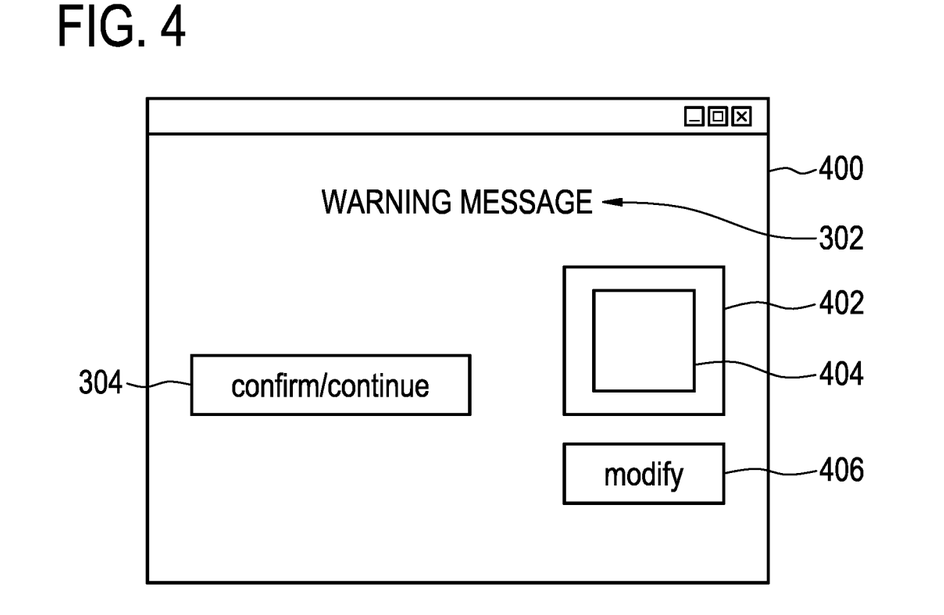
FIG. 4 illustrates a further example of a graphical user interface.

FIG. 4 shows a further example of a metadata parameter correction box or a scan parameter correction box 400. Again, this box 400 shows the warning message 302. In both FIGS. 3 and 4 the warning message 302 may contain information which is provided to the operator which may warn the operator that either the metadata and/or the scan parameters are incorrect or need to be checked. The box 400 again shows the control 304. In contrast box 400 shows a data entry box 402 where one or more values of metadata or scan parameters can be changed by the operator. In this example the data entry box 402 is also shown as initially containing a suggested value or values 404. This may be useful for the operator in selecting the proper values. The box 400 is further shown as containing a modify button 406. When the modify button 406 is clicked the current value of the data entry box 402 is submitted to change the metadata and/or the configuration data.

Figure 5:
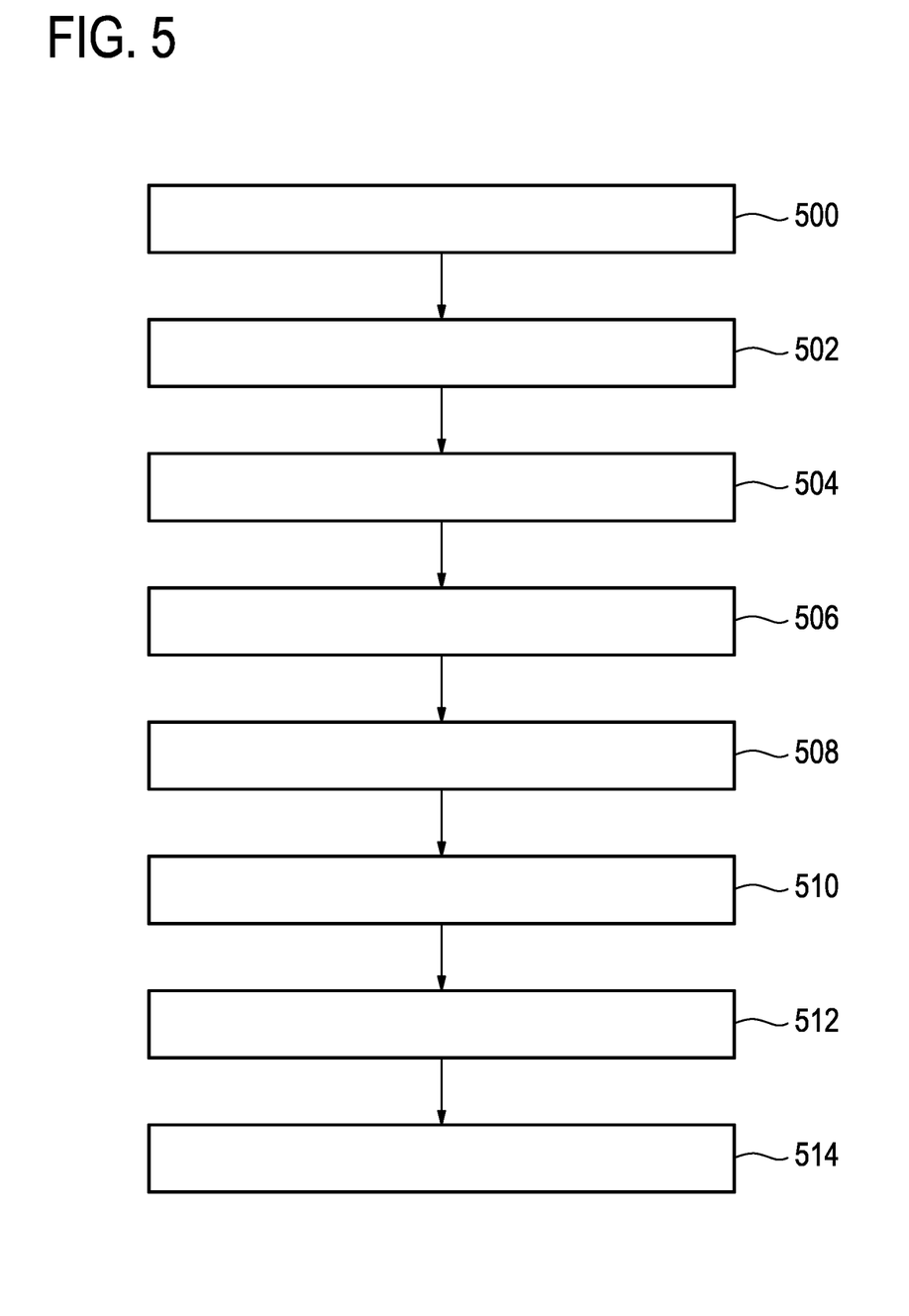
FIG. 5 shows a flow chart that illustrates a method of operating the magnetic resonance imaging system of FIG. 1 or FIG. 2.

FIG. 5 shows a flowchart which illustrates a method of operating the magnetic resonance imaging system 100 of FIG. 1 or the magnetic resonance imaging system 200 of FIG. 2. First, in step 500, scan parameter data 146 is received. The scan parameter data 146 may be for modifying the behavior of the pulse sequence commands 142. Next, in step 502, the metadata 148 descriptive of imaging conditions are received from the user interface 132. Then, in step 504, the configuration data 150, 250, 252, 254 is stored in the memory 134. Then in step 506 the error probability 152 is calculated by comparing the metadata 148, the configuration data 150, and the scan parameter data 146 using the predefined model 154. The error probability may be descriptive of a deviation or difference or inconsistency between the metadata 148 and between the configuration data 150 and/or the scan parameter data 146. Next, in step 508, a predetermined action 158 is performed if the error probability 152 is above the predetermined threshold 156. Then, in step 510, the magnetic resonance imaging system is controlled to acquire the magnetic resonance data 144 from the subject 118. Step 512 is then performed. A response 160 is received from the user interface 132 in response to the signal 158. Step 512 may be performed before, after or during the execution of step 510. Finally, in step 514, the one or more magnetic resonance images 162 is reconstructed from the magnetic resonance data 144. In some examples, the magnetic resonance image 162 may also include corrected metadata 148.

Figure 6:
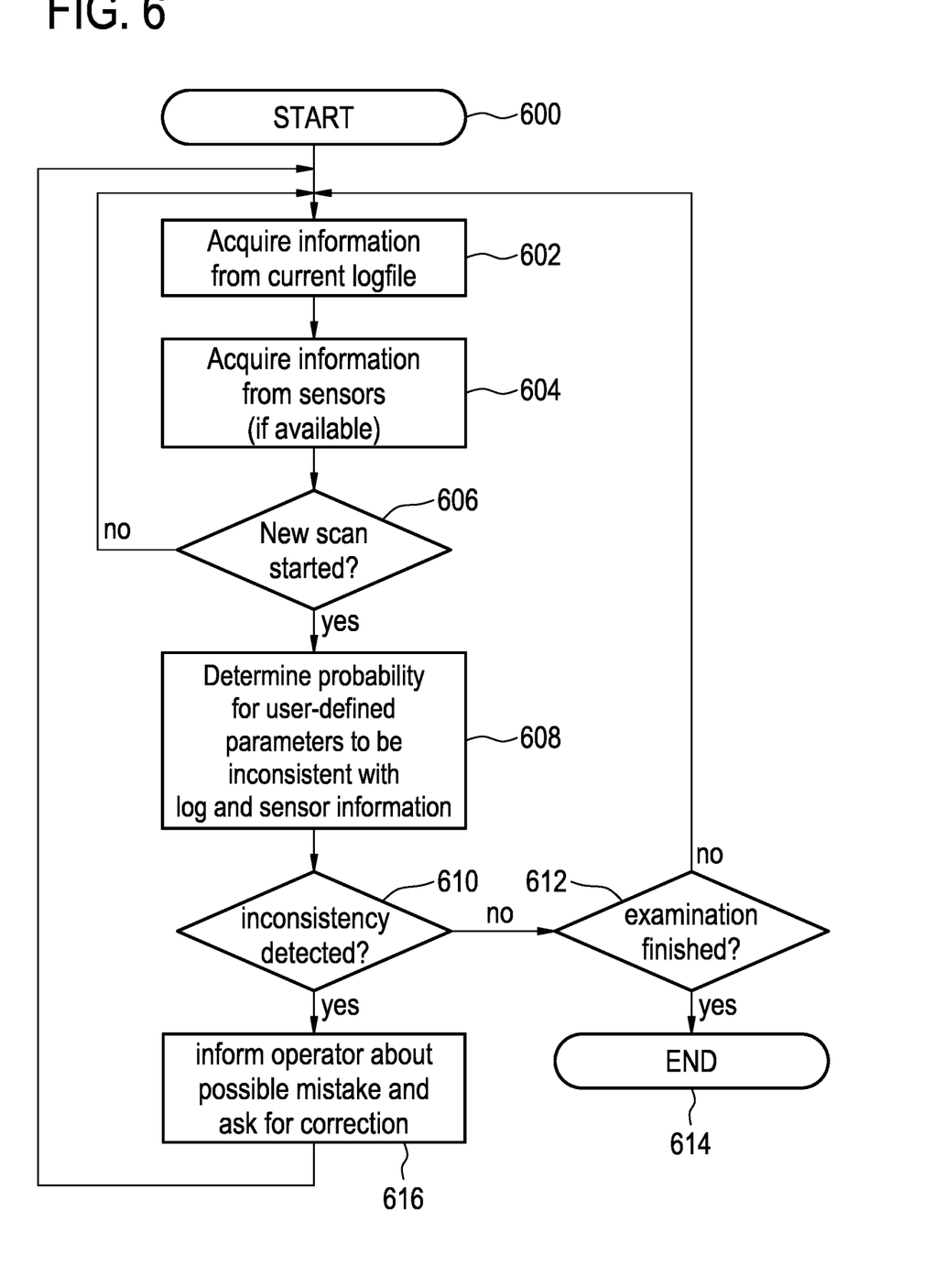
FIG. 6 shows a flow chart that illustrates a further method of operating the magnetic resonance imaging system of FIG. 1 or FIG. 2.

FIG. 6 shows a flowchart which illustrates an alternate method of operating the magnetic resonance imaging system 100 of FIG. 1 or the magnetic resonance imaging system 200 of FIG. 2. The features of FIGS. 5 and 6 may be combined. In some examples the features or steps in FIG. 6 are equivalent to steps performed in FIG. 5.

The method in FIG. 6 starts in step 600. Step 600 is labeled start, the method starts here. The method then proceeds to step 602. In step 602 information is acquired from the current log file of the magnetic resonance imaging system. Next in step 604 information from sensors if they are available is acquired. Step 602 and step 604 are equivalent to step 504 of the method shown in FIG. 5. Examples of sensors in step 604 would be the camera 202, weight sensor, or from the subject support actuator 206. After step 604 the method proceeds to step 606. Step 606 is a decision box and the question is a new scan started. If the answer is no the method proceeds back to step 602. If the answer is yes then the method proceeds to step 608. In step 608 a probability for a user to find parameters to be inconsistent with the log and sensor information is performed. Step 608 is equivalent to step 506 in FIG. 5. It should be noted that the data from the current log file 602 in FIG. 6 may have several different means depending upon the example. The data in the log file may represent both scan parameter data 146 and/or configuration data 150. In some instances step 602 may also represent receiving the scan parameter data 500.

After step 608 has been performed the method proceeds to decision box 610. The question in step 610 is an inconsistency detected. Step 610 may be equivalent to calculating the error probability and then comparing it to the predetermined threshold 156. If no inconsistency is detected the method proceeds to step 612. Step 612 is again a decision box. The question is the examination finished. If the answer is no, the method proceeds back to step 602. If the examination is finished, the method proceeds to step 614 which is marked end, the method ends here. Returning to decision box 610 if an inconsistency is detected the method proceeds to step 616. In step 616 the operator is informed of a possible mistake and is asked for a correction. Step 616 may be equivalent to steps 508 and 512. After step 616 is performed the method returns back to step 602.

Examples may relate to quality control in radiologic data acquisition. Medical images (e.g. in DICOM format) contain lots of metadata, describing anatomy, position, patient-specific information, or other parameters. Some of this information must or can be entered manually when medical images are acquired, which represents a source of error. This invention describes a method to automatically check the plausibility of image metadata and to interact with the operator of a medical imaging device in real time, whenever a disagreement or inconsistency is found.

Quality control of clinical processes is of increasing importance. This concerns not only the quality of diagnosis and treatment, but also the quality of documentation. A lot of data is still entered manually and is therefore susceptible to errors. Even if not all information can be obtained automatically, in some cases a plausibility check is still possible. This invention relates to automated plausibility checks of radiological metadata.

Medical images (e.g. in DICOM format) contain lots of metadata, describing anatomy, position, patient-specific information, or other parameters. Some of this information must or can be entered manually when medical images are acquired, which represents a source of error. Statistical analyses, quality management, or reimbursement management may be affected by incorrect, missing or inconsistent image metadata.

Examples may provide for a means of automatically checking the plausibility of image metadata already during the examination, based on information obtained from different sources, such as machine log files and sensors at the imaging equipment.

At the same time, the proposed method can act as a quality control mechanism to prove that any inconsistencies have been checked.

Examples may have one or more of the following features:

A plausibility check algorithm (a predefined model) that uses information from machine logs and sensor information to determine a probability that metadata entered by the operator is correct An interactive user interface (a user interface) that warns the operator if any piece of metadata is likely to be incorrect and proposes to change the entry A flowchart of an example method is presented above in FIG. 6. Internal machine data (e.g., extracted from log files in real time) and sensor data (e.g., camera information) are continuously acquired. As soon as a new scan is started (i.e., the setting is fixed), a logic algorithm estimates the most probable values for the different image metadata fields. The estimation logic can be based on pre-defined rules set by domain experts or on rules derived from training data using machine learning techniques. If machine learning is employed, rules can be updated continuously using the collected sensor data and the values entered by the technician, after correction, as training data.

Examples for information obtained from logfiles (configuration data) or other system data (in real time) may include one or more of the following:

Patient table position

Connected MR coil type

Scan name entered by operator (may contain abbreviations for contrast agent etc.)

Applied dose for CT or X-ray systems with automatic dose control

Geometry information from survey or scout scans

Examples for information obtained from optional sensors may include one or more of the following:

Patient position and orientation on table (determined by camera)

Patient weight (estimated by 3D-camera or measured by weighing setup in patient table)

Examples of functions of the predefined model may include one or more of the following features:

Estimation of body part: From patient table position and connected coil type estimate for which body part most probably MRI images are being acquired. Examples: If a head coil is used, the anatomic region is probably "head" or "brain", while other anatomic regions are very unlikely. If a flexible coil array is used and the patient table is not completely inserted into the bore, a scan of the lower extremities is more probable than a scan of the abdomen. If survey/surview or scout images are available, body parts can also be identified from these using known object recognition methods. Other sensors or information could contribute information about the body part: Breath hold scans or respiration triggering using a respiration belt indicate an abdominal scan. When vector ECG (VCG) electrodes are used, the scan is most likely a cardiac scan.

Estimation of scan/exam name plausibility: Based on additional information like respiration-triggered or breath-hold scans and/or associated sensors used like respiration belt or VCG Estimation of contrast agent probability: Typical contrast agent examinations for MRI imaging include T1 and T2 imaging pre-contrast, and T1 post-contrast. If a table motion and delay are detected after a T1 scan and another T1 scan is executed afterwards, it is likely that contrast agent has been administered. Any scan following a contrast-enhanced scan must necessarily also be a post-contrast scan.

Head-first or feet-first: This information can be induced by camera images or by coil and table settings. Usage of a head coil with only the inner part of the table moved into the bore hints at a head-first configuration.

Patient age: A very course estimate of the patient age can be achieved by analysis of camera images or table position. It is possible to distinguish a child from a grown-up.

Patient weight: The patient weight can be estimated from 3D camera images or measured by a sensor in the patient table. Furthermore, the weight can be checked against the patient age, e.g., it is unlikely that a 5-year-old patient weighs 90 kg. For X-ray-based systems with automatic dose control, the weight can be cross-checked against the applied dose. If a high dose has to be applied in order to achieve a certain detector signal, it is unlikely that the patient is very slim.

These estimates are then compared with the data entered found in the metadata fields of the images.

Examples for image metadata that may be entered manually may include one or more of the following:
  Scanned anatomic region
  Patient direction (head first/feet first)
  Patient age
  Patient weight
  Image with/without contrast agent
  Type of examination (scan/exam name)

Whenever an inconsistency is detected, the operator may receive a message and is being asked to either correct the information to be stored in the image metadata, or to acknowledge that the information is really correct.

In one example, user interaction is requested only during scanning operation, when the operator is not handling the patient or performing other tasks. In this way, interference of the user interaction request with the imaging workflow is minimized.

In one example, the system will only continue when the operator has either corrected or acknowledged the correctness of the piece of information in question. In this way, a quality assurance mechanism is installed, because it can be proved that any inconsistency in the data has been checked by the operator.

In one example, the interactive user interface not only asks for a correction, but also proposes the most probable value for the piece of information in question (if available).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
102 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
136 network interface
140 machine executable instructions
142 pulse sequence commands
144 magnetic resonance data
146 scan parameter data
148 metadata
150 configuration data
152 error probability
154 predefined model
156 predetermined threshold
158 commands to generate signal
160 response from user interface
162 magnetic resonance image
150 configuration data
202 camera
204 weight sensor
206 subject support actuator
250 camera data
252 weight sensor data
254 table position data
260 workstation
262 segmentation algorithm
264 image segmentation
300 metadata parameter correction box or scan parameter correction box
302 warning message or signal
304 control to confirm accuracy
306 control to abort scan
308 control to open interface to modify data 400 metadata parameter correction box or scan parameter correction box
402 data entry box
404 suggested value
406 control to submit value in data entry box
500 receive scan parameter data for modifying the behavior of the medical imaging system commands
502 receive metadata descriptive of imaging conditions from the user interface
504 store configuration data descriptive of a current configuration of the medical imaging system in the memory
506 calculate an error probability by comparing the metadata, the configuration data, and the scan parameter data using a predefined model
508 perform a predefined action if the error probability is above a predetermined threshold
510 control the medical imaging system to acquire the medical image data from a subject
512 receive a response to the signal from the user interface in response to the signal
514 reconstruct one or more medical images from the magnetic resonance data in accordance with the response
600 start
602 Acquire information from current logfile
604 Acquire information from sensors (if available)
606 New scan started?
608 Determine probability for user-defined parameters to be inconsistent with log and sensor information
610 inconsistency detected?
612 examination finished?
614 end
616 inform operator about possible mistake and ask for correction

The invention claimed is:

1. A medical imaging system for acquiring medical image data from an imaging zone, the medical imaging system comprising:
a memory for storing machine executable instructions and medical imaging system commands, wherein the medical imaging system commands are configured for controlling the medical imaging system to acquire the medical image data according to a medical imaging protocol;
a user interface;
a processor for controlling the medical imaging system, wherein execution of the machine executable instructions cause the processor to:
receive scan parameter data that specify the imaging protocol for modifying the behavior of the medical imaging system commands, the scan parameter data specifying the imaging protocol;
receive metadata descriptive of imaging conditions from the user interface;
store configuration data descriptive of a current configuration of the medical imaging system in the memory, the configuration data being descriptive of the actual mechanical and electrical configuration of the medical image system;
calculate an error probability by comparing the metadata, the configuration data, and the scan parameter data using a predefined model, wherein the error probability is descriptive of an error among the metadata, the configuration data and the scan parameter data, and the predefined model represents how metadata, configuration data and scan parameter data form correct combinations or represents likelihoods of such combinations being correct or incorrect;
perform a predefined action if the error probability is above a predetermined threshold, wherein the predetermined action comprises providing a signal to notify the user;
control the medical imaging system to acquire the medical image data from a subject;
receive a response to the signal to notify the user from the user interface in response to the signal; and
reconstruct one or more medical images from the medical image data in accordance with the response.

2. The medical imaging system of claim 1, wherein the predefined action comprises displaying a metadata parameter correction box on the user interface, and wherein the metadata parameter correction box comprises a prompt to correct at least a portion of the metadata.

3. The medical imaging system of claim 2, wherein execution of the machine executable instructions cause the processor to display the metadata parameter correction box before acquisition of the medical image data and/or during acquisition of the medical image data.

4. The medical imaging system of claim 2, wherein computation of the error probability comprises comparing a subject orientation in the metadata and an orientation determined from the configuration data.

5. The medical imaging system of claim 2, wherein computation of the error probability comprises comparing an anatomic region specification in the metadata and an anatomic region determined from the configuration data.

6. The medical imaging system of claim 2, wherein execution of the machine executable instructions cause the processor to display a set of suggested metadata corrections in the metadata parameter correction box.

7. The medical imaging system of claim 1, wherein the predefined action comprises displaying a scan parameter correction box on the user interface, wherein the scan parameter correction box comprises a prompt to correct at least one scan parameter, and wherein execution of the machine executable instructions cause the processor to display the scan parameter correction box before acquisition of the medical image data.

8. The medical system of claim 7, wherein execution of the machine executable instructions cause the processor to display a set of suggested scan parameter corrections in the scan parameter correction box.

9. The medical imaging system of claim 1, wherein the imaging conditions of the metadata comprises at least one of: a subject orientation of the subject, a subject age of the subject, a subject weight of the subject, specification if the medical image was acquired with or without a contrast agent, a scan type of the medical imaging protocol, and a scan name of the medical imaging protocol.

10. The medical imaging system of claim 1, wherein the current configuration of the medical imaging system of the configuration data comprises at least one of:
connected coil type;
an image of a body position of the subject;
a fiducial marker position of a fiducial marker on the subject;
weight sensor data descriptive of the weight of the subject;
data from survey magnetic resonance image or scout magnetic resonance image of the subject;
an applied dose for a CT or an X-ray system for irradiating the subject;
a subject weight of the subject; and
a subject support position of a subject support of the medical imaging system.

11. The medical imaging system of claim 1, wherein the one or more medical images comprises the metadata.

12. The medical imaging system of claim 1, wherein the predefined model is at least one of: a decision tree, a statistical likely hood model, principal components analysis model, a machine learning model, and a neural network.

13. The medical imaging system of claim 1, wherein the medical imaging system comprises at least one of: a magnetic resonance imaging system, an X-ray machine, a computed tomography system, a PET system, and a SPECT system.

14. A non-transitory computer readable medium comprising machine executable instructions for execution by a processor controlling a medical imaging system, wherein the medical imaging system is configured for acquiring medical data from an imaging zone, wherein the medical imaging system comprises a user interface, and wherein execution of the machine executable instructions cause the processor to:
   receive scan parameter data for modifying the behavior of medical imaging system commands, wherein the medical imaging system commands are configured for controlling the medical imaging system to acquire the medical image data according to a medical imaging protocol, the scan parameter data specifying the imaging protocol;
   receive metadata descriptive of imaging conditions from the user interface;
   store configuration data descriptive of a current configuration of the medical imaging system in a memory, the configuration data being descriptive of the actual mechanical and electrical configuration of the medical image system;
   calculate an error probability by comparing the metadata, the configuration data, and the scan parameter data using a predefined model, wherein the error probability is descriptive of an error among the metadata, the configuration data and the scan parameter data, and the predefined model represents how metadata, configuration data and scan parameter data form correct combinations or represents likelihoods of such combinations being correct or incorrect;
   perform a predefined action if the error probability is above a predetermined threshold, wherein the predetermined action comprises providing a signal to notify the user;
   control the medical imaging system to acquire the medical image data from a subject;
   receive a response from the user interface in response to the signal; and
   reconstruct one or more medical images from the medical image data in accordance with the response.

15. A method of operating a medical imaging system, wherein the medical imaging system is configured for acquiring medical image data from an imaging zone, wherein the medical imaging system comprises a user interface, a memory for storing machine executable instructions, and a processor, and wherein execution of the machine executable instructions cause the processor to:
   receive scan parameter data for modifying the behavior of medical imaging system commands, wherein the medical imaging system commands are configured for controlling the medical imaging system to acquire the medical image data according to a medical imaging protocol, the scan parameter data specifying the imaging protocol;
   receive metadata descriptive of imaging conditions from the user interface;
   store configuration data descriptive of a current configuration of the medical imaging system in the memory, the configuration data being descriptive of the actual mechanical and electrical configuration of the medical image system;
   calculate an error probability by comparing the metadata, the configuration data, and the scan parameter data using a predefined model, wherein the error probability is descriptive of an error among the metadata, the configuration data and the scan parameter data, and the predefined model represents how metadata, configuration data and scan parameter data form correct combinations or represents likelihoods of such combinations being correct or incorrect;
   perform a predefined action if the error probability is above a predetermined threshold, wherein the predetermined action comprises providing a signal to notify the user;
   control the medical imaging system to acquire the medical image data from a subject;
   receive a response from the user interface in response to the signal; and
   reconstruct one or more medical images from the medical image data in accordance with the response.

* * * * *